(12) United States Patent
Mertens et al.

(10) Patent No.: US 9,791,385 B2
(45) Date of Patent: Oct. 17, 2017

(54) MODULAR HIGH RESOLUTION X-RAY COMPUTED TOMOGRAPHY SYSTEM

(71) Applicants: James C. E. Mertens, Tempe, AZ (US); Jason J. Williams, Scottsdale, AZ (US); Nikhilesh Chawla, Tempe, AZ (US)

(72) Inventors: James C. E. Mertens, Tempe, AZ (US); Jason J. Williams, Scottsdale, AZ (US); Nikhilesh Chawla, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 415 days.

(21) Appl. No.: 14/556,714

(22) Filed: Dec. 1, 2014

(65) Prior Publication Data

US 2015/0160354 A1    Jun. 11, 2015

Related U.S. Application Data

(60) Provisional application No. 61/914,106, filed on Dec. 10, 2013.

(51) Int. Cl.
*G01N 23/00* (2006.01)
*A61B 6/00* (2006.01)
*G01N 23/04* (2006.01)

(52) U.S. Cl.
CPC .................... *G01N 23/046* (2013.01)

(58) Field of Classification Search
CPC .................................................. G01N 23/046
See application file for complete search history.

(56) References Cited

U.S. PATENT DOCUMENTS 6,104,776 A * 8/2000 Oikawa ................. G01N 23/06
378/10
7,215,736 B1   5/2007 Wang et al.

OTHER PUBLICATIONS

Dudek et al., "Three-dimensional (3D) microstructure visualization of LaSn3 intermetallics in a novel Sn-rich rare-earth-containing solder," Materials Characterization, ISSN 1044-5803, 2008, vol. 59, Issue 9, pp. 1364-1368.
Williams et al., "Damage evolution in SiC particle reinforced Al alloy matrix composites by X-ray synchrotron tomography," Acta Materialia, ISSN 1359-6454, 2010, vol. 58, Issue 18, pp. 6194-6205.
Padilla et al.,"Quantifying the effect of porosity on the evolution of deformation and damage in Sn-based solder joints by X-ray microtomography and microstructure-based finite element modeling," Acta Materialia, ISSN 1359-6454, 2012, vol. 60, Issue 9, pp. 4017-4026.

(Continued)

*Primary Examiner* — Dani Fox
(74) *Attorney, Agent, or Firm* — Quarles & Brady LLP

(57) ABSTRACT

A modular X-ray computed tomography (XCT) system having a higher degree of modularity provides experimental versatility and in situ capabilities. The modular XCT system includes interchangeable X-ray sources and detectors that allow for the XCT system to be readily adapted to different imaging tasks, such as those that may require different trade-offs between spatial resolution, exposure time, power, and other scanning parameters.

20 Claims, 9 Drawing Sheets

(56) References Cited

OTHER PUBLICATIONS

Flynn et al., "Microfocus X-ray sources for 3D microtomography," Nuclear Instruments & Methods in Physics Reasearch Section A: Accelerators, Spectrometers, Detectors and Associated Equipment, ISSN 0168-9002, 1994, vol. 353, Issue 1-3, pp. 312-315.
Feldkamp et al., "Practical cone-beam algorithm," Journal of the Optical Society of America, ISSN 1084-7529, 1984, vol. 1, Issue 6, pp. 612-619.
Schena et al., "Detecting microdiamonds in kimberlite drill-hole cores by computed tomography," International Journal of Mineral Processing, ISSN 0301-7516, 2005, vol. 75, Issues 3-4, pp. 173-188.
Uhlmann et al., "Characterization and comparison of direct and indirect converting X-ray detectors for non-destructive testing (NDT) in low-energy and high-resolution applications," Nuclear Instruments and Methods in Physics Research Section A: Accelerators, Spectrometers, Detectors and Associated Equipment, ISSN 0168-9002, 2008, vol. 591, Issue 1, pp. 46-49.
Koch et al., "X-ray imaging with submicrometer resolution employing transparent luminescent screens," Journal of the Optical Society of America, ISSN 1084-7529, 1998, vol. 15, Issue 7, pp. 1940-1951.
Uesugi et al., "Comparison of lens- and fiber-coupled CCD detectors for X-ray computed tomography," Journal of Synchrotron Radiation, ISSN 0909-0495, 2011, vol. 18, Issue 2, pp. 217-223.
Dierick et al., "The use of 2D pixel detectors in micro- and nano-CT applications," Nuclear Instruments and Methods in Physics Research Section A: Accelerators, Spectrometers, Detectors and Associated Equipment, ISSN 0168-9002, 2008, vol. 591, Issue 1, pp. 255-259.
Packham D. (2010). "Testing and Characterisation of Scintillator Materials for X-ray Detection." Master's thesis, University of Surrey, Surrey, UK.
Schena et al., "Conceiving a high resolution and fast X-ray CT system for imaging fine multi-phase mineral particles and retrieving mineral liberation spectra," International Journal of Mineral Processing, ISSN 0301-7516, 2007, vol. 84, Issues 1-4, pp. 327-336.
Mueller et al., "Anti-aliased three-dimensional cone-beam reconstruction of low-contrast objects with algebraic methods," IEEE Transactions on Medical Imaging, ISSN 0278-0062, 1999, vol. 18, Issue 6, pp. 519-537.
Taylor et al., "Resolution, artifacts and the design of computed tomography systems," Nuclear Instruments and Methods in Physics Research Section A: Accelerators, Spectrometers, Detectors and Associated Equipment, ISSN 0168-9002, 1986, vol. 242, Issue 3, pp. 603-609.
Masschaele et al., "UGCT: New X-ray radiography and tomography facility," Nuclear Instruments and Methods in Physics Research Section A: Accelerators, Spectrometers, Detectors and Associated Equipment, ISSN 0168-9002, 2007, vol. 580, Issue 1, pp. 266-269.
Martin et al., "Recent developments in X-ray imaging with micrometer spatial resolution," Journal of Synchrotron Radiation, ISSN 0909-0495, 2006, vol. 13, Issue 2, pp. 180-194.
Sato et al., "Development of a high-resolution x-ray imaging system with a charge-coupled-device detector coupled with crystal x-ray magnifiers," Review of Scientific Instruments, ISSN 0034-6748, 2000, vol. 71, Issue 12, pp. 4449-4456.
Tous et al., "High-resolution X-ray imaging CCD camera based on a thin scintillator screen," Radiation Measurements, ISSN 1350-4487, 2007, vol. 42, Issues 4-5, pp. 925-928.
Graafsma et al., "Detectors for Synchrotron Tomography," Advanced Tomographic Methods in Materials Research and Engineering, Edited by J. Banhart, (Oxford Scholarship Online, 2008), pp. 227.
Aslund et al., "Detectors for the future of X-ray imaging," Radiation Protection Dosimetry, ISSN 0144-8420, 2010, vol. 139, Issues 1-3, pp. 327-333.
Valais et al., "Comparative evaluation of single crystal scintillators under x-ray imaging conditions," Journal of Instrumentation, ISSN 1748-0221, 2009, vol. 4, Issue 6, pp. P06013.
Williams et al., "On the Correlation Between Fatigue Striation Spacing and Crack Growth Rate: A Three-Dimensional (3-D) X-ray Synchrotron Tomography Study," Metallurgical and Materials Transactions A: Physical Metallurgy and Materials Science, ISSN 1073-5623, 2011, vol. 42, Issue 13, pp. 3845-3848.
Williams et al., Characterization of Damage Evolution in SiC Particle Reinforced Al Alloy Matrix Composites by In-Situ X-Ray Synchrotron Tomography, Metallurgical and Materials Transactions A: Physical Metallurgy and Materials Science, ISSN 1073-5623, 2011, vol. 42, Issue 10, pp. 2999-3005.
Stampanoni et al., "High resolution X-ray detector for synchrotron-based microtomography," Nuclear Instruments and Methods in Physics Research Section A: Accelerators, Spectrometers, Detectors and Associated Equipment, ISSN 0168-9002, 2002, vol. 491, Issues 1-2, pp. 291-301.
Mertens et al., "Development of a lab-scale, high-resolution, tube-generated X-ray computed-tomography system for three-dimensional (3D) materials characterization," Materials Characterization, ISSN 1044-5803, Jun. 2014, vol. 92, pp. 36-48.

* cited by examiner

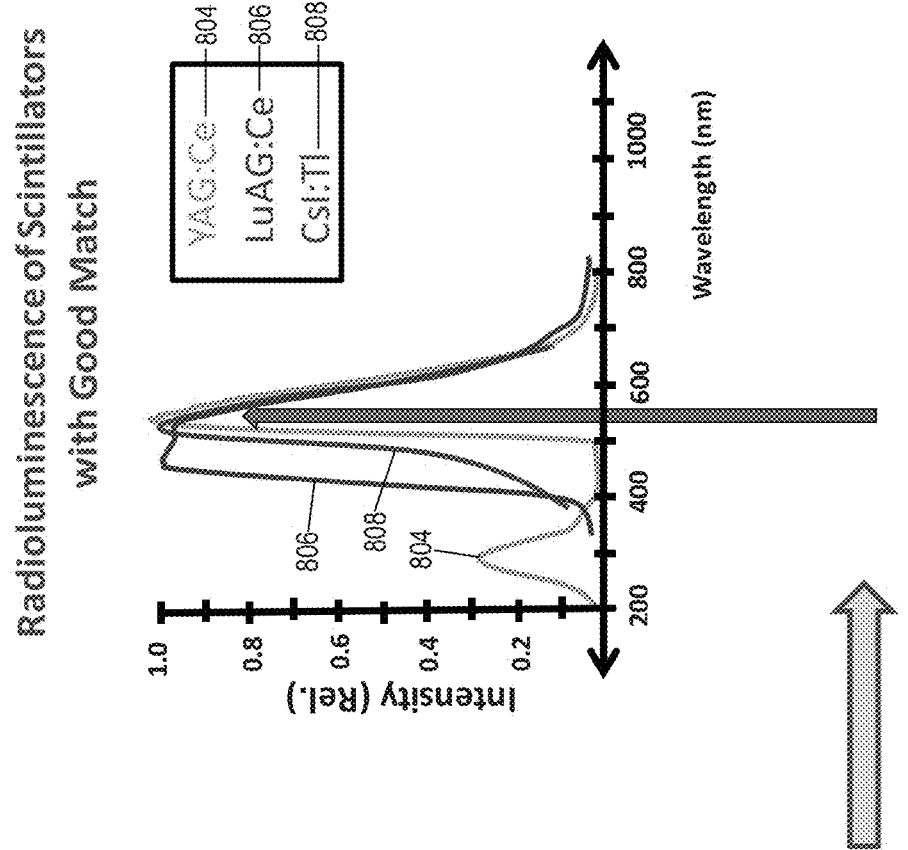
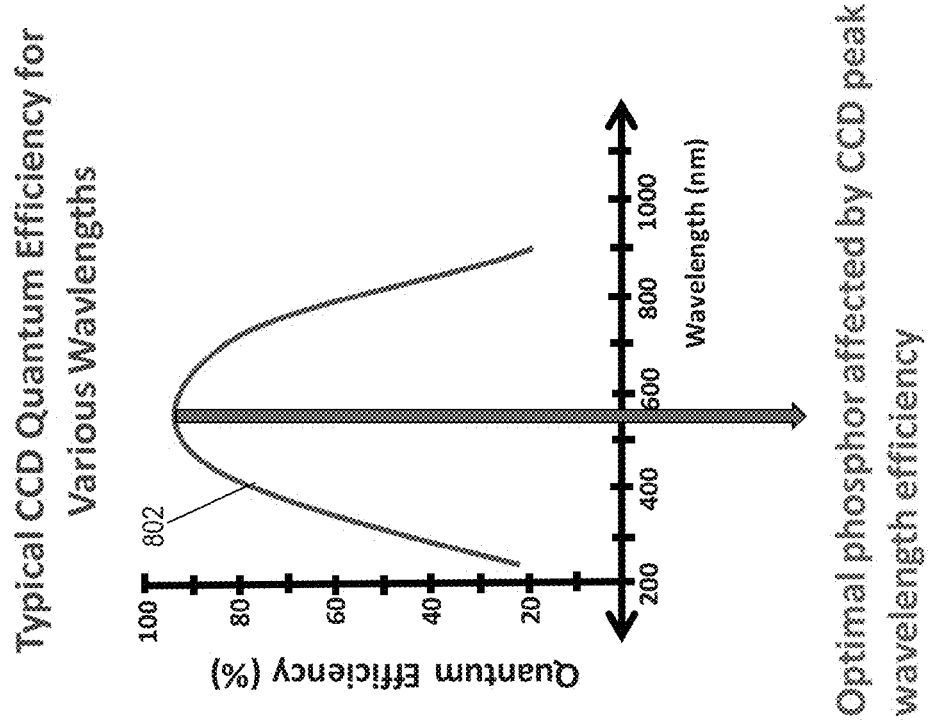
Fig. 8B
Fig. 8A

MODULAR HIGH RESOLUTION X-RAY COMPUTED TOMOGRAPHY SYSTEM

CROSS-REFERENCE TO RELATED APPLICATIONS

This application is based on, claims priority to, and incorporates herein by reference in its entirety U.S. Provisional Application Ser. No. 61/914,106, filed Dec. 10, 2013, and entitled, "MODULAR HIGH RESOLUTION X-RAY COMPUTED TOMOGRAPHY SYSTEM."

BACKGROUND OF THE INVENTION

The field of the invention is systems and methods for X-ray computed tomography (CT). More particularly, the invention relates to a modular X-ray CT system.

Three-dimensional (3D) imaging of material microstructures has typically been limited to destructive techniques, such as serial-sectioning. In more recent times, the nondestructive approach of X-ray micro-computed tomography (XCT) has demonstrated unique 3D imaging capabilities in the study of microstructures and material behavior phenomena. XCT techniques have long been used in the medical field, but they have become increasingly applicable to materials science research as the achievable imaging resolution has approached a scale suitable to study material microstructures. Select research facilities currently employ synchrotron light sources in XCT experiments (e.g., Beamline 2BM, Advanced Photon Source, Argonne National Laboratories); these laboratories are expensive, limited in number, and in high demand, thereby requiring users to run experiments over short time frames and at low frequencies. Accordingly, lab-scale devices (e.g., Xradia, Inc., CA, USA; Bruker Corporation, WI, USA) have been commercially developed for quality control and even research, allowing manufacturers to non-destructively inspect parts for flaws, and to quickly perform failure analysis.

Bench-top systems have fallen short of synchrotron facilities primarily due to the nature of the X-ray source. In-house XCT systems utilize braking radiation derived X-rays, rather than synchrotron derived X-ray beams. These bench-top systems use a less brilliant, polychromatic cone beam rather than a highly brilliant, monochromatic parallel beam. The reduced brilliance affects the necessary scan time, whereas the conic polychromatic beam leads to image artifacts that must be corrected. The resolution of these in-house systems has been limited by, among other issues, the X-ray source and detector limitations.

It is understood that advances in components for X-ray generation and imaging are continually advancing in performance, further bridging the gap between synchrotron imaging. However, these advances are slow to arrive in commercial systems. Furthermore, it would be desirable to have systems with a larger range of functionality in terms of sample size and imaging resolution that can be accommodated, complete control over the trade-off between imaging resolution and detection efficiency, a higher degree of component modularity for component versatility, and a capacity to accommodate a wide range of in situ experimental apparatuses.

SUMMARY OF THE INVENTION

The present invention overcomes the aforementioned drawbacks by providing a modular X-ray computed tomography (XCT) system. The modular XCT system includes a base, an interchangeable X-ray source coupled to the base, a sample rotation stage coupled to the base, an X-ray detection system coupled to the base, and at least one computing system in communication with the X-ray detection system. The interchangeable X-ray source is configured to emit an X-ray beam towards a sample positioned in the X-ray computed tomography system. The interchangeable X-ray source is one of a plurality of different X-ray sources configured to be interchangeably coupled to the base. The sample rotation stage is configured to receive a sample and to position the sample within a field-of-view of the interchangeable X-ray source. The X-ray detection system includes at least one interchangeable X-ray detector configured to acquire data as X-rays impinge on the X-ray detector, wherein the at least one interchangeable X-ray detector is one of a plurality of different X-ray detectors configured to be interchangeably coupled to the electronic sensor in the X-ray detection system. The X-ray detection system also includes a port configured to receive the at least one interchangeable X-ray detector, light scintillating medium. The at least one computing system is configured to receive two-dimensional projection data from the X-ray detection system and to reconstruct multiple, unique, and continuous 2D images of the sample's X-ray attenuating volume therefrom.

In one aspect of the invention, the one or more X-ray detectors may include a scintillator and/or a photon counting detector. Scintillator in this context refers to any material or device which produces photons of a lower energy than the absorbed X-rays, regardless of absorption efficiency, where the number produced is dependent on the incident X-ray photon's intensity.

In another aspect of the invention, the X-ray detection system may be configured as a refraction or reflection-based lens-coupled system, in which a lens is optically coupling the electronic sensor to the one or more scintillating X-ray detectors.

In another aspect of the invention, the X-ray detection system may be configured as a fiber optically-coupled system, in which a fiber optic assembly is optically coupling one or more of the photo-electronic sensor elements to the one or more scintillating X-ray detectors.

In another aspect of the invention, a method of image reconstruction using a modular X-ray computed tomography system is provided. The method includes receiving a sample on a sample rotation stage coupled to a base, and positioning the sample on the sample rotation stage within a field-of-view of an interchangeable X-ray source. The method further includes emitting, from the interchangeable X-ray source, an X-ray beam towards a sample positioned in the X-ray computed tomography system. The interchangeable X-ray source is one of a plurality of different X-ray sources configured to be interchangeably coupled to the base. Data is acquired, using at least one interchangeable X-ray detector coupled to the base, as X-rays impinge on the X-ray detector. The at least one interchangeable X-ray detector is one of a plurality of different X-ray detectors configured to be interchangeably coupled to a X-ray detection system. Data is received, using at least one computing system in communication with the X-ray detection system, from the X-ray detection system to reconstruct an image of the sample therefrom.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 8A-B are exemplary views of quantum efficiency and intensity plotted against wavelength for different scintillators;

DETAILED DESCRIPTION OF THE INVENTION

Described here is a modular X-ray computed tomography (XCT) system having a higher degree of modularity, which provides experimental versatility and in situ capabilities. The modular XCT system includes interchangeable X-ray sources and detectors that allow for the XCT system to be readily adapted to different imaging tasks, such as those that may require different trade-offs between spatial resolution, exposure time, power, and other scanning parameters.

Figure 1:
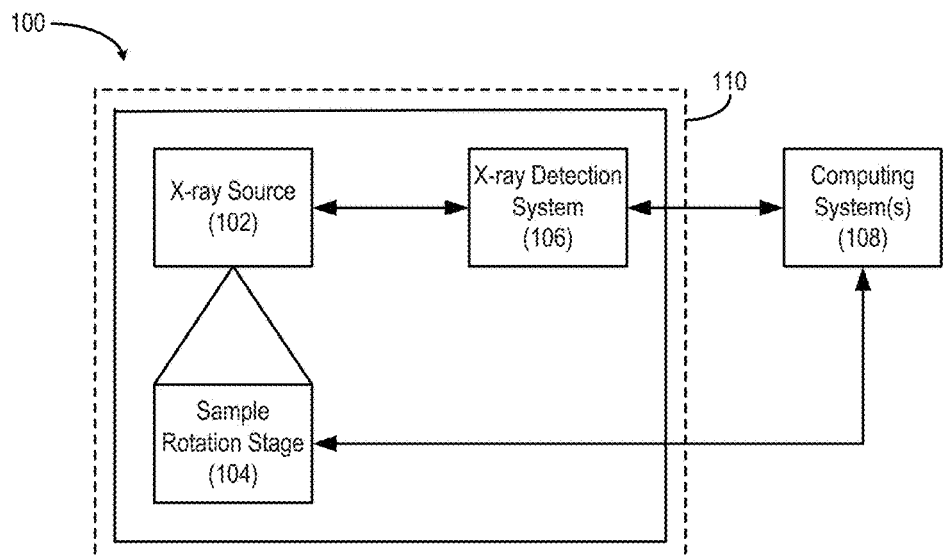
FIG. 1 is a diagrammatic view of an XCT system.

Referring to FIG. 1, a modular three- and four-dimensional XCT system 100 is shown. The XCT system 100 includes an X-ray source 102, a sample rotation stage 104, an X-ray detection system 106, and at least one computing system 108 for controlling data acquisition software and equipment, performing raw image calibration, performing reconstruction algorithms, and performing post-reconstruction image processing for microstructural segmentation, visualization, and quantification. The XCT system 100 may also include shielding 110 around the apparatus to contain high energy radiation produced during nondestructive imaging. In one non-limiting example, the thickness of the shielding 110 may be designed to reduce the highest energy X-rays of the highest intensity possibly emitted from the X-ray source 102 to safe exposure levels. A vibration-damping breadboard table top (not shown) and air-floating vibration isolator support columns may be used as the foundation of the system components to shield the sensitive components of the XCT system 100 from environmental vibrations.

In some embodiments, the X-ray source 102 is one that emits parallel, monochromatic X-rays, such as synchrotron beam-lines. This type of X-ray beam readily allows for determining the actual linear X-ray attenuation coefficient in a voxel, whereas, with an untreated X-ray tube, such accuracy is made more difficult by the polychromatic nature of the X-ray beam.

The selection of an X-ray source 102 for high resolution imaging is preferably a microfocus X-ray source capable of emitting X-rays from a micrometer-sized target area. Parameters to consider when selecting the X-ray source 102 include the power range; the voltage range; focal spot size as a function of power; the minimum focus-to-object (FOD) distance which can limit X-ray flux through the sample; the type of target; the target's composition; whether the target is cooled, rotated, or interchangeable; the lifetime of the X-ray tube in the case of a vacuum sealed source, or the lifetime of the filament in the case of a vacuum-pumped source; the maneuverability and compatibility with the system design; and the cost of the X-ray source.

In some embodiments, the X-ray source 102 can be the model XWT-160-SE/TC X-ray source sold by X-RAY WorX GmbH. This source is capable of 160 kV of accelerating potential, yielding high energy X-rays to maximize transmission through large samples. The X-ray source 102 may also be capable of a very small focal spot size for high resolution imaging, and has dual-target (transmission and reflection) interchangeability to perform multi-scale imaging. The X-ray source 102 is also capable of achieving a minimum detail detectability of less than about 0.3 micrometers and maximum power of about 3 W with the high resolution transmission target, and a minimum detail detectability of less than about 2.0 micrometers and a maximum power of about 280 W with the reflection target.

Figures 2A, 2B:
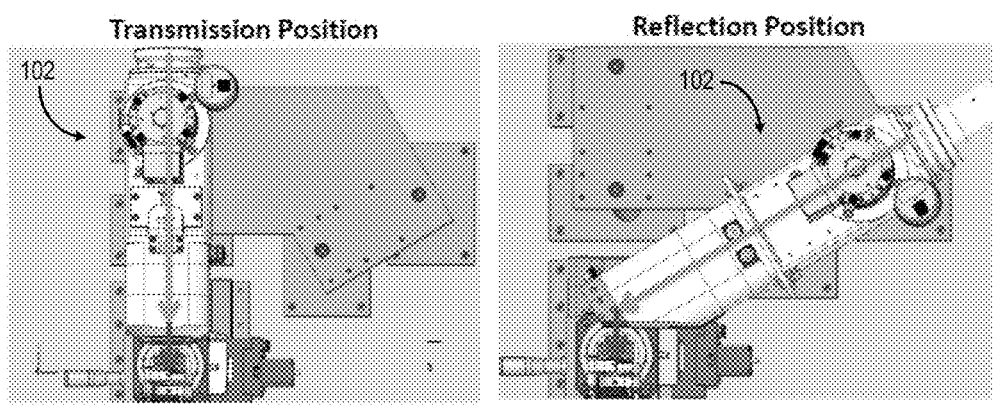
FIGS. 2A-B are top perspective views of two exemplary X-ray source configurations to be implemented into the XCT system of FIG. 1.

Referring now to FIGS. 2A and 2B, the transmission and reflection configurations, respectively, of this example X-ray source are shown. One advantage of the XCT system 100 is that the X-ray source 102 is capable of more than one configuration. Different X-ray source 102 configurations may be used depending on the particular imaging task. The implications of using a transmission type configuration are that a potentially smaller focal spot and a better resolution are achievable at the expense of beam intensity, implying a longer exposure or less signal for a given sample. The implications of using a reflection type configuration are that it has a larger minimum focal spot and a larger minimum spatial resolution, but can achieve a relatively higher beam intensity implying shorter exposures, or more signal for a given sample. The transmission configuration may be used for a lower power target, while the reflection configuration may be used for a higher power target.

Some embodiments may use a different X-ray source than the one described above. One advantage of the XCT system 100 of the present invention is that the X-ray source 102 is easily interchangeable and upgradable, depending on the requirements of the particular imaging task.

The sample rotation stage 104 preferably rotates without any physical distortion and provides precise and accurate positioning of the sample being imaged. In some embodiments, the rotation stage 104 may include the ORT-101-L Air Rotary Air Bearing with a Delta Tau MAC-MC-1A-SD Controller. This example configuration may be selected because it does not compromise the imaging resolution of the XCT system 100 and because it provides about a 27 kg load capacity, high positioning precision within about 0.00001 degrees, and low distortions of less than about 0.25 µm at about 11 rpm 6 inches from the spindle face.

Figure 3:
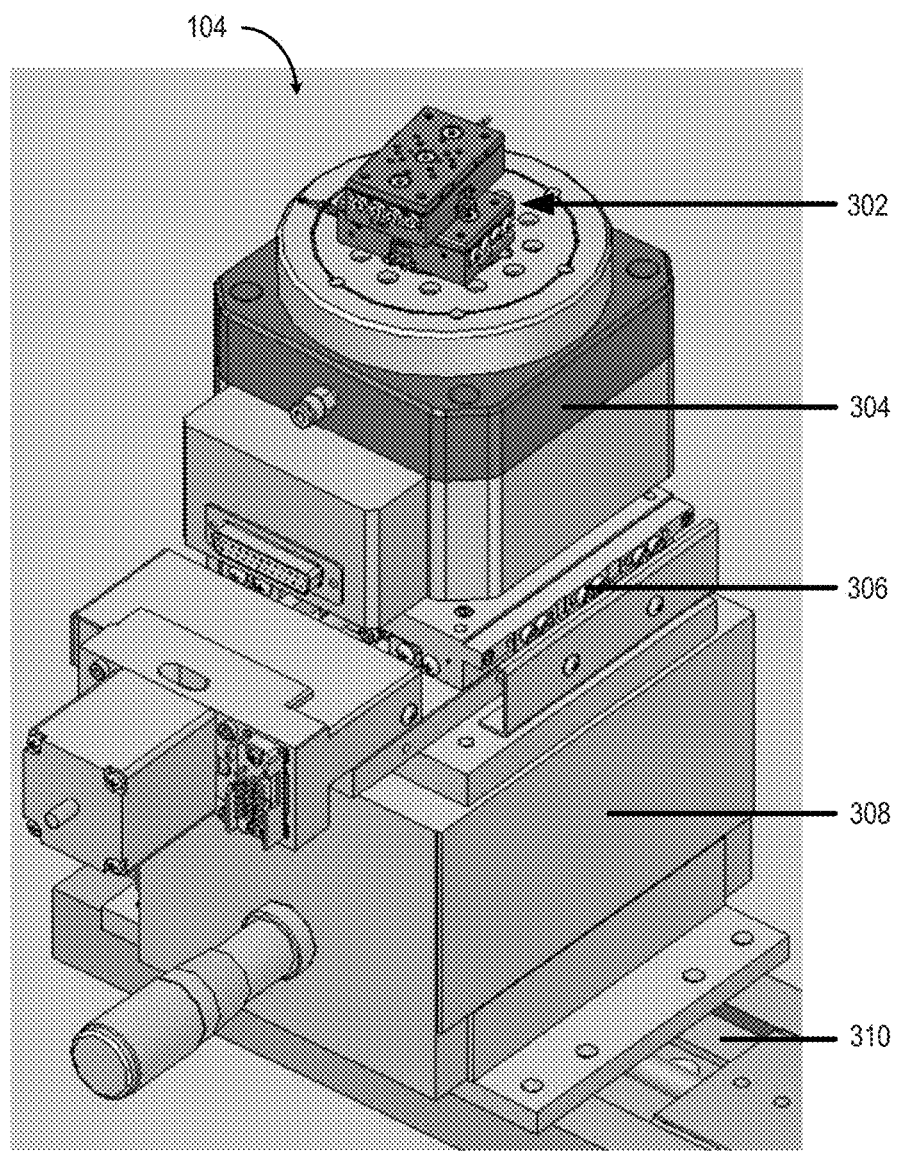
FIG. 3 is a perspective view of an exemplary X-ray rotation stage to be implemented into the XCT system of FIG. 1.

Referring now to FIG. 3, centering the sample to be imaged on the center of the sample rotation stage 104 may be necessary to maximize the field of view, in order to minimize the resolution achievable for a given sample region-of-interest dimension. In some embodiments, two linear-axis piezo centering stages of approximately 5 kg load capacity and about 2 nm resolution can be implemented to center the sample on the rotation stage 104. Long-range linear stages may also be used when obtaining reference images and for aligning and positioning the sample and X-ray detection system 106 with each other and the central axis of the X-ray beam.

X and Y centering stages 302 center the sample on the rotation stage 104 to maximize the field of view and increase resolution. The X and Y centering stages 302 may have a high load capacity and high precision. An air-bearing rotary stage 304 rotates the sample to acquire images for tomography reconstruction. The air-bearing rotary stage 304 may have a high load capacity, may be accurate for reconstruction fidelity, and may have a fully programmable controller. A transverse beam direction stage 306 may also be provided for rotation-to-source and detector-axis alignment and for acquiring flat field reference images. The transverse beam direction stage 306 may be fully programmable and highly repeatable. A height adjustment stage 308 aligns the imaging field of view with the region of interest vertically. The height adjustment stage 308 may be heavy duty and high-precision for accommodating experimental cell/sample size variation. A beam-axis translation stage 310 may be provided for magnification and field of view control. The beam-axis translation stage 310 may be long range, micron sensitive, and heavy duty.

Although some embodiments have a sample rotation stage 104 configured as described above, it will be appreciated that other embodiments may use a different sample rotation stage. One advantage of this XCT system 100 is that the sample rotation stage 104 is easily interchangeable and upgradable, depending on the requirements of the particular imaging task.

Figure 4A:
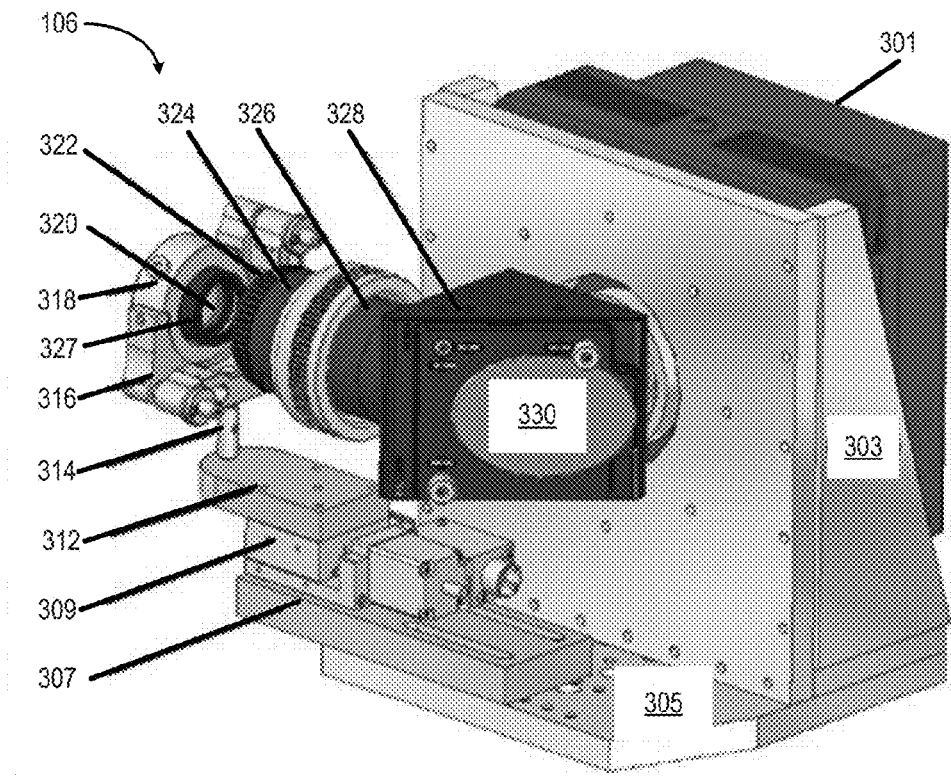
FIGS. 4A-B are perspective views of an exemplary X-ray detection system to be implemented into the XCT system of FIG. 1.
Figure 4B:
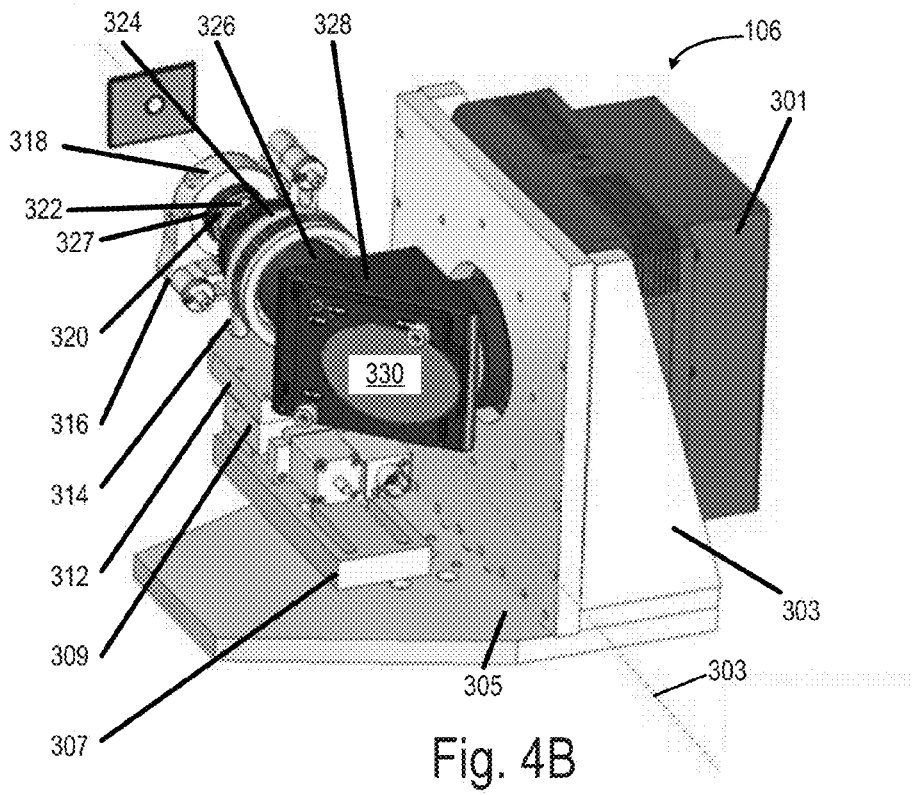

Referring now to FIGS. 4A and 4B, the X-ray detection system 106 may include a camera 301, a camera support bracket (not shown) and shield 303 (also designed to support the scintillator), a base plate 305, a long-range extension plate 307 for changing extension tubes, a focusing stage 309, a mirror-mount-to-focusing-stage adapter 312, a mirror-mount post 314, a mirror mount 316, a shaft collar support 318 for an optical tube assembly 320, a bellows material 322 (visually excluded for clarity), a lens 324, extension tubes and adjust length collar 326, a right-angle mirror housing 328, and a right-angle mirror 330. Considerations for the design of the X-ray detection system 106 include field of view, X-ray resolution and focal spot size, X-ray magnification, lens magnification, lens resolving power, scintillator resolution, X-ray detection efficiency.

The computing system 108 of FIG. 1 may include, for example, two workstations implemented in the system 100 to increase the flow of data. One of the workstations may be utilized to control data acquisition software and equipment, and the second workstation may be utilized for raw image calibration, running reconstruction algorithms, and performing post-reconstruction image processing for microstructural segmentation, visualization, and quantification, for example. In one non-limiting example, the performance specifications of the reconstruction-algorithm running workstation include a central processing unit (CPU) that utilizes an Intel Core i5-2500K 3.3 GHz quad-core processor (Intel Corporation, CA, USA) for the reconstruction of the 3D volume. The system may employ a 448 core 6 GB CUDA enabled GPU (Tesla c2075, NVIDIA Corporation, CA, USA) for the graphic hardware accelerated reconstruction, for example.

For performing reconstruction on large datasets without the use of a computer cluster, the size of the RAM on the computing system 108 may be about 32 gigabytes (GB). In some embodiments, roughly twice the projection data set, in single precision, plus 5-10 GB may be required to run cone-beam reconstructions, that is, without breaking the data up into smaller subsets. For example, a 1441 image dataset (i.e., ⅛° steps over 180°) acquired using 2048×2048 elements per frame is roughly 22.5 GB, making it necessary to reconstruct such a large dataset in subsets. The workstation used for data acquisition may primarily acts as a scan control station, using routines written in LabVIEW, for example, from National Instruments Corporation, to communicate with the X-ray source 102, CCD camera 301, four linear axes, and rotations axis.

Figure 5A:
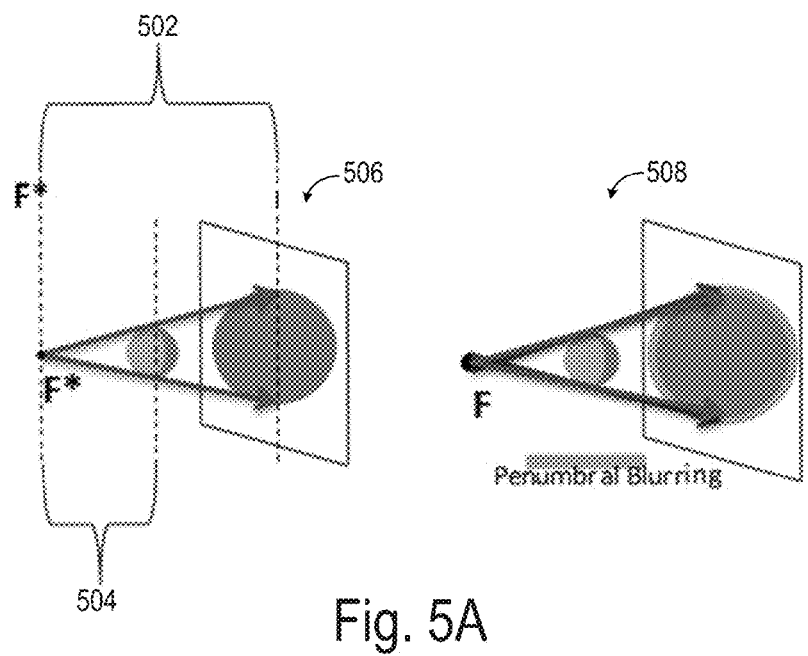
FIG. 5A shows exemplary views an X-ray point source model and a finite X-ray source model for finding the system magnification.
Figure 5B:
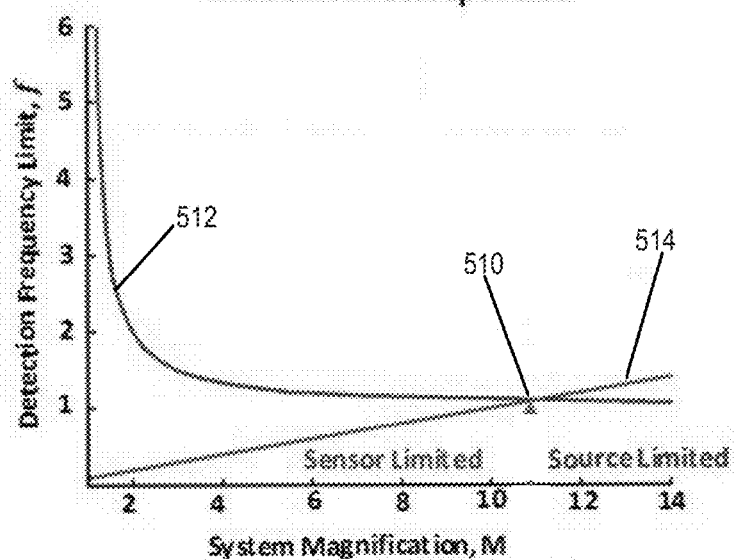
FIG. 5B is a graph showing a spatial frequency limit for a given detector pixel size and source focal spot size.

Referring now to FIGS. 5A and 5B, the magnification of the X-ray source 102 and the magnification of the X-ray detection system 106, respectively, are shown. The magnification of the X-ray source 102 may be measured based on the source-to-detector distance (SDD) 502 and the source-to-axis of rotation distance (SAD) 504 as shown using the ideal X-ray point source model 506 and the finite X-ray source model 508. The magnification of X-ray source 102 can be obtained from equations (1) and (2) below:

$$M_{Total} = M_{Optical} * M_{x\text{-}ray} \tag{1}$$

$$M_{x\text{-}ray} = \frac{SDD}{SAD} \tag{2}$$

where $$M_{x\text{-}ray} = \frac{M_{Total}}{M_{Optical}} = \frac{SDD}{SAD}.$$

The total magnification of the X-ray detection system 106 can be shown by finding an intersection 510 of a source focal spot size curve 512 and a pixel size curve 514, as shown in FIG. 5B, represented by equations 3 and 4, respectively, below:

$$f = \frac{M}{F(M-1)} \tag{3}$$

$$f = \frac{M}{3*p} \tag{4}$$

with a focal spot size of about 1 μm and a pixel size of about 5 μm, making the total magnification of the XCT system 100 equal to equation 5 below:

$$M_{Total} = \frac{2p}{F} + 1 \tag{5}$$

In one non-limiting example, the determination of the system magnification, X-ray generating target configuration (transmission vs. reflection), the X-ray tube accelerating voltage, and the X-ray target current to achieve a particular targeted spatial resolution can be acquired using equation (1)

above. The system magnification required to reach a certain resolution can be determined from a sensor pixel size, and the focal spot size can then be determined without limiting resolution. The X-ray accelerating voltage, target current, and target type can be adjusted to achieve the focal spot size. The focal spot size of the X-ray source 102 may be considered as a function of target power or X-ray intensity in conjunction with the desired imaging goals. The achievable X-ray magnification may be limited by the component separation distances (i.e., SDD and SAD), the size of the X-ray detecting screen and the camera's 301 FOV.

In some embodiments, the X-ray detection system 106 may implement a configuration where the electronic sensor is lens-coupled to the scintillator, however, it may be possible to use other configurations, such as a direct X-ray imaging sensor configuration or a configuration where the electronic sensor is fiber-optically coupled to a scintillator. An example of each of these configurations will now be described in brief.

Figure 6A:
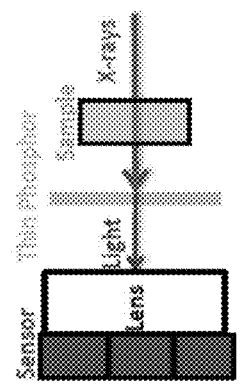
FIGS. 6A-C are diagrammatic views of three possible X-ray detection system configurations.
Figure 6B:
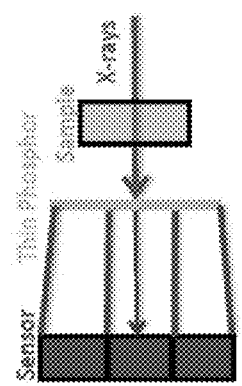
Figure 6C:
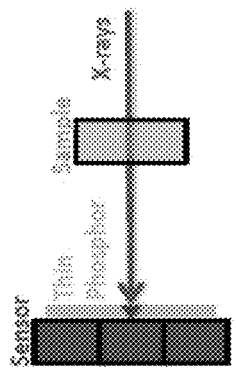

Referring now to FIGS. 6A-C, each X-ray detection system 106 configuration has different implications. A lens-coupled configuration, such as the one shown in FIG. 6A, possesses a variable optical magnification. Another implication of using the lens-coupled configuration is that the optical design and support thereof need be considered before adoption. In the lens-coupled configuration, the X-ray derived signal can be directed away from the X-ray beam in order to reduce X-ray noise in the acquired data. The X-ray noise may be caused by interaction of the detection sensor with non-signal X-rays, using any optical method including surface reflection, as performed with the mirror 330 shown in FIGS. 4A-B.

Figure 7:
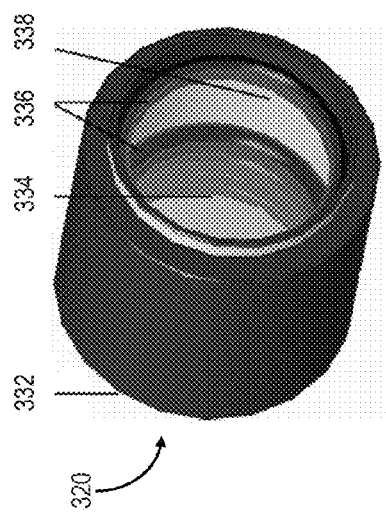
FIG. 7 is an enlarged perspective view of the exemplary optical tubing assembly of FIGS. 4A-B.

Specific to the lens-coupled configuration shown in FIG. 6A, in addition to installing the right-angle mirror 330 in the optical path, the optical tubing assembly 320 is also configured to contain at least one optical-window-X-ray-stop 327 (see FIGS. 4A-B) both anterior and posterior to the optical mirror, that is a material or assembly which passes optical light with high efficiency while simultaneously attenuating undesired X-rays in the optical path. The current realization of this design may be achieved using, for example, 6 mm thick leaded-glass windows of a high surface smoothness and parallelism, held in place using optical retaining rings 336 via the internal threading of optical tubes 332 of the optical tube assembly 320, as best shown in FIG. 7. Applicable to either lens-coupled or fiber-coupled detector configurations, X-ray noise can further limited in the detector by the installation of an X-ray beam field-limiting aperture either between the X-ray source and the sample, or between the sample and the detector, or both. By minimizing the X-ray beam emission, past the aperture, to a narrow solid angle which is constrained by the condition of containing the entire sample region-of-interest, the number of X-rays which can interact with the detector's digitization medium is further reduced. The system's current realization of the field-limiting aperture may be achieved by physical insertion of a ¼inch thick lead panel, for example, wherein a hole is machined through the entire thickness, and the hole is aligned with the X-ray-source-sample-detector axis 340, and the plate is positioned along this axis to minimize the X-ray emission solid angle as previously described.

A fiber-optically coupled configuration, such as the one shown in FIG. 6B, may have high transfer efficiency and can bend in order to divert the X-ray derived signal away from the non-signal X-ray beam to inhibit image noise, resulting in a similarly beneficial solution for this consideration as the lens-coupled configuration of FIG. 6A. Another implication of using the fiber-optically coupled configuration is that the alignment and mounting of the configuration exhibit more of a fixed configuration in terms of optical magnification, but more flexible in terms of its physical spatial positioning depending on the flexibility and slack in the optical-fibers.

A direct X-ray imaging panel configuration, such as the one shown in FIG. 6C, is condensed and has low maintenance. Other implications of using a direct X-ray imaging panel are the typically lower resolution and no magnification control.

The camera 301 chosen for some embodiments is the Apogee Alta U230 with a high cosmetic-grade large format (2048×2048 pixel) back-illuminated CCD array composed of 15 μm square pixels, a 16-bit digital dynamic range, and a peak quantum efficiency of about 95% at 550 nm, corresponding to the peak emission spectra of LuAG:Ce (cerium-doped lutetium aluminum garnet), YAG:Ce (cerium-doped yttrium aluminum garnet), and CsI:Tl (thallium doped cesium iodide), approximately. FIGS. 8A and 8B show the typical CCD quantum efficiency for various wavelengths as well as radioluminescence of scintillators with a good match, respectively. More specifically, FIG. 8A shows quantum efficiency with a midband coating 802 and the optimal phosphor wavelength affected by CCD peak wavelength efficiency. FIG. 8B shows how the different scintillators, namely, YAG:Ce 804, LuAG:Ce 806, and CsI:Tl 808 match up with that optimal phosphor wavelength. The lens 324 selected for some embodiments is the Schneider Optics Micro-Symmar 2.8/50 mm. This lens is a finite-focus macro-lens selected on imaging resolution, a relatively large numeric aperture, low image distortion and magnification variability. As a finite-focus lens, the magnification of the lens system may be tailored by altering the length of the optical track length to the chip, which also changes to working distance of the lens. Thus, the lens' image quality may be optimized for a magnification factor of 3.5×, for example. The optical track length may be adjusted using the adjustable length optical tube 332, or alternatively by adding or removing optical extension tubes.

Although some embodiments make use of the camera 301 and lens 324 configurations described above, it will be appreciated that other embodiments may use a different camera and lens. One advantage of the XCT system 100 of the present disclosure is that the camera 301 and lens 324 are easily interchangeable and upgradable, depending on the requirements of the particular imaging task.

Referring back to FIG. 7, the optical tube assembly 320 may include an optical tube 332, a scintillator 334, retaining rings 336, and a Kapton film sealing front 338. The optical tube 332 may provide a stable support for the scintillator 334 and provide alignment capability for rotation and pitch to realize a scintillator 334 that is perpendicular to both the central beam of the X-ray source 102 and the camera 301 and lens 324 assembly. The optical tube 332 may also adjust the spacing between the scintillator 334 and the camera lens 324.

The scintillator 334 and its supporting substrate may be mounted within the optical tube 332 between two low stress retaining rings 336. If a supporting substrate is used for the scintillator 334, this should be mechanically rigid and optically transparent. In some embodiments, the substrate should be optically transparent behind the majority of the central portion of the scintillator's active area. It is undesirable that environmental particulates settle on any surface of any optically sensitive components, thus it becomes necessary to create a contained environment for the optical components of the detector 106. The front of the optical tube 332 may be sealed off, for example, by a 0.001 inch thick layer of Kapton film 338, pinned to the front of the optical tube 332 with a third retaining ring (not shown). The back of the optical tube 332 may be effectively sealed by the back of the scintillator 334 substrate. In the event the scintillator 334 is a freestanding component without a substrate, supported only by the retaining rings, the substrate can be replaced with an optical-window-X-ray-stop (not shown), in order to pass the optical signal while simultaneously attenuating undesirable X-rays effectively reducing any noise caused by their interaction with the detector's 106 signal digitizing medium. The optical tube 332 may be optically sealed at the front by a graphite spray, for example, and in the back by the bellows material (not shown) linking the optical tube 332 to the lens 324. The graphite spray may be used to inhibit dust from settling on the scintillator 334 surface and to inhibit dead zones in the X-ray detection system 106.

The optical tube assembly 320 and contained scintillator 334 may be mounted within the shaft collar support 318, as shown in FIGS. 4A and 4B, to adjust pitch. The optical tube assembly 320 may be incorporated into the full X-ray detection system 106. Another linear stage may also be implemented to focus the optical system on the scintillator 334. In one preferred embodiment, the linear stage may have a 10 mm travel range with 2 µm of travel per motor step sufficient for focusing. Longer travel ranges may be enabled by a custom slider plate, for example. The focusing stage 309 may be mounted on the custom slider plate.

The considerations for selecting a scintillator 334 may be, but are not limited to, material composition, thickness, emission spectra, and density and light yield for maximizing detection efficiency over a range of X-ray energy balanced against factors such as the thickness, index of refraction, and numeric aperture of the lens system for high resolution imaging capability. The scintillator 334 selected for one preferred embodiment is a single crystal LuAG:Ce circular disk, selected based on achievable resolution, the resulting detector quantum efficiency with the camera and lens, and commercial availability in a wide range of thicknesses. The scintillator 334 may be of varying thicknesses for different uses. While LuAG:Ce has been chosen for the preferred embodiment, any appropriate scintillator 334 is interchangeable in the system 100. One advantage of this XCT system 100 is that the scintillator 334 is easily interchangeable and upgradable, depending on the requirements of the particular imaging task. In some embodiments, scintillator screens may also be used to achieve a higher imaging resolution.

Having described the general configuration of an XCT system 100 in accordance with some embodiments of the present invention, a description of an example operation of the XCT system 100 is now provided. Data is acquired from a sample using the XCT system 100. The projections acquired using the XCT system 100 are saved for processing and image reconstruction. For the data acquisition, the increment of the sample stage rotation may be set along with the number of projections to acquire at each orientation, the range of the rotation, the length of each exposure, the pixel binning parameter (the square root of the number of physical pixels grouped together for electronic readout, in order to maximize signal at the loss of resolution), the number of reference and dark images desired, and the destination path. Images may be calibrated by programs on a scan workstation using, for example, the following equation:

$$CP = \frac{RP - MDF}{MRF - MDF}; \quad (6)$$

where CP is the calibrated projection, RP is the raw projection, MDF is the master dark frame, and MRF is the master reference frame. It will be appreciated that other algorithms, such as ones that determine a closest matching reference frame, measured in either time of acquisition or similarity of pixel value magnitudes in the pixel field, rather than an average from the entire bank of reference images, can also be used. Other algorithms might include noise reduction techniques which acquire multiple raw projections (RP) of the same orientation and determine which pixels and in which frames contain erroneous X-ray signal, replacing these pixel's values with the corresponding pixel value from other projections of the orientations, and then averaging all projections of the same orientation. The flat frames, or reference frames, may be taken under the same conditions as the sample projections, but with no sample in the path between beam and detector. Because X-ray noise may be present, and is essentially random in spatial detection, dark frames are acquired with the X-ray beam off so as to account for electronic sensor background including thermal contributions.

Normalizing each projection by a flat frame may deconvolute the true X-ray signal from the background signal in the imaging system, such as vignetting (i.e., a natural slight dimming at the corners of the square chip coupled with a circular lens) or hot pixel (i.e., pixels which generate a higher than average number of electrons per incident photon) response. The dark frames are ideally taken at the same temperature as the projections, with the same exposure length, and are subtracted from light and reference frames to remove count contributions from thermal and electronic noise. These frames are taken with the beam on and the camera shutter closed. The term 'master' is used to imply that several of each type of correction frame may be taken and averaged for the correction of each projection. In some embodiments, negative values can result from the subtraction in either the numerator or the denominator, and that 16-bit integer values usually become decimalized values upon division. The negative values may be coerced to zero and the decimal values may be stored as 32-bit real values to maintain precision, but not be as memory intensive as double precision values. These calibrated projections are then transferred to a reconstruction workstation for post-processing.

Image reconstruction can be performed using any number of known reconstruction algorithms, such as fast-Fourier-transform back-projection algorithms. As one example, the Feldkamp, Davis, and Kress ("FDK") method can be used for image reconstruction. This can be accomplished through a collection of different programming languages and programming software, and either computed on one or more central-processing-units or using multiple cores of one or more programmable graphic-processing-units.

Figure 9:
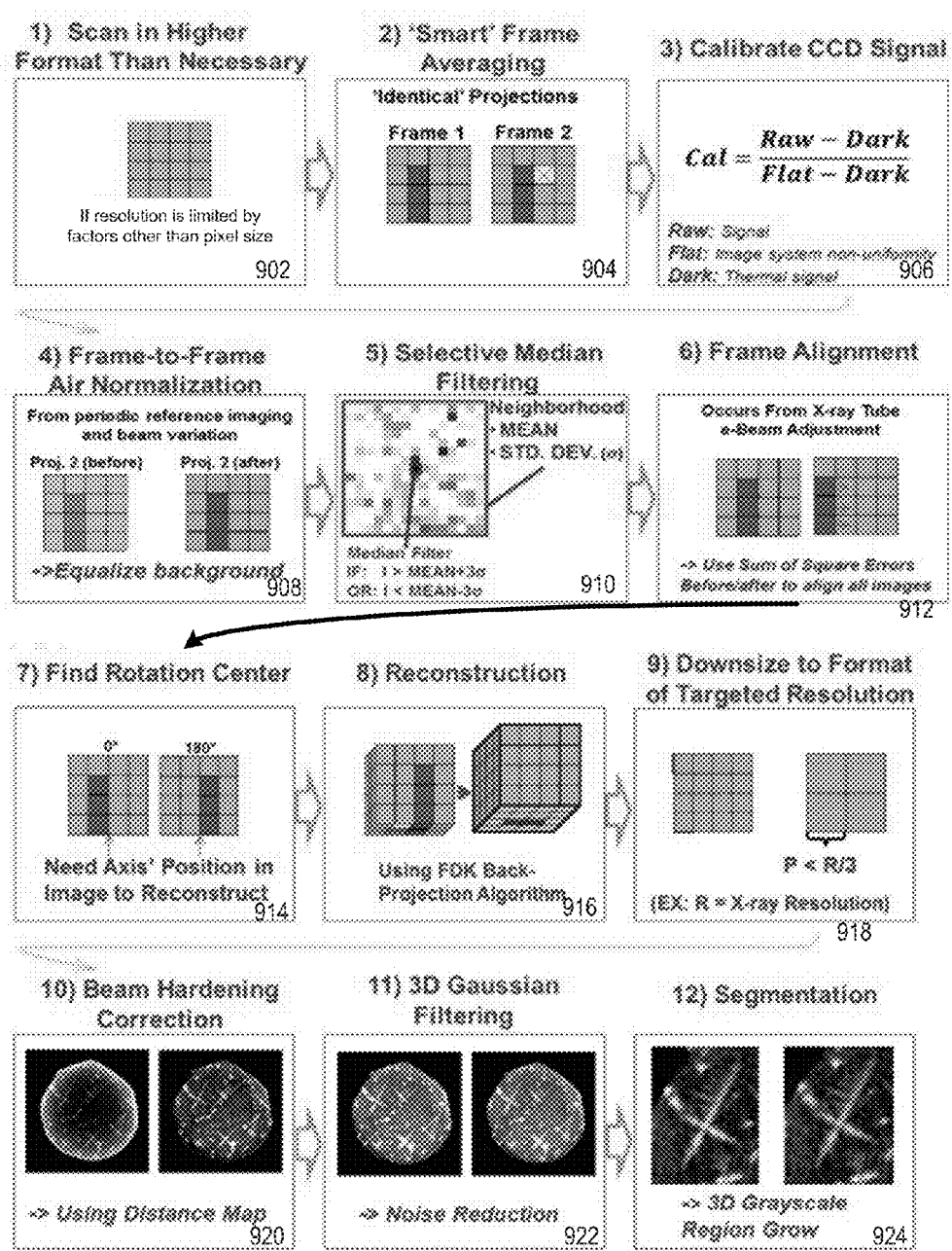
FIG. 9 is a flowchart setting forth exemplary steps of a method for data processing of an X-ray image.

Referring now to FIG. 9, an example of a method for data processing in the XCT system 100 is shown. The above processing steps are provided with the realization that the application of X-ray computed is most generally performed with the intention or ultimate goal of achieving a segmented dataset of the various distinct phases which are resolved in the grayscale three-dimensional reconstruction derived from the reconstruction algorithm when applied to the acquired two-dimensional radiographs acquired at unique sample orientations during the scan. The first six steps (i.e., steps 902, 904, 906, 908, 910, and 912) deal with improving the quality of the projection input into the reconstruction algorithm to effectively increase to quality of the reconstruction, and the last six steps (i.e., steps 914, 916, 918, 920, 922, and 924) regard processing the reconstruction for volume analysis, or more specifically for feature segmentation.

In FIG. 9, the 'acquired format' refers to the number pixels which are present in the acquired image, which can be controlled during acquisition by setting a pixel-binning parameter. For example, in the case of the realized prototypes current digital sensor, the 2048×2048 element sensor can acquire images in the full 2048×2048 format, which corresponds to a binning parameter of 1. By setting the binning parameter to 2, each exclusive 2×2 array of imaging sensors in the imaging chip is treated as a single element, resulting in an image which contains an image array of 1024×1024 pixels. One cannot increase the image format beyond the physical arrangement of physical sensors, but can decrease the format by binning. The reason that binning be applied during acquisition can be one of many possible benefits: Decreased data size, increased counts per pixel element, increased image readout, and accelerated processing.

To perform binning without degrading the image resolution, the actual resolution in the image must be limited by some other factor than pixel size, for example, X-ray focal spot penumbra or the spatial resolution of the scintillator 334 itself. The first step of the outlined processing workflow is to acquire a higher than necessary image format, if possible, as indicated in step 902. The reason for doing so is to maintain a higher degree of object fidelity when performing pixel-based processing in the succeeding steps.

The second step of the proposed processing regards the mechanism of the acquisition of the object's X-ray projection, in order to eliminate any X-ray noise that is present after taking precautions to remove the imaging sensor from the X-ray path in the detector design, as indicated in step 904. Rather than take a single exposure of the object's X-ray projection at a given orientation, at least two projections are acquired of the object at the same orientation.

The at least two projections can then be compared to determine which pixels (i,j), and in which projection, contain undesired X-ray noise. This is performed by first making three assumptions, 1) the X-ray noise is perfectly random, 2) the interaction of the X-ray with the sensor causes an increase in the counts acquired at that pixel, and 3) an X-ray interacting with the same pixel in two different projections is highly unlikely and ignored. If the two projections acquired are P1 and P2, for example, one can look at the comparison image, COMP, to make the correction. If, COMP=P1/P2, and COMP(i,j)>(1+Tolerance), then the pixel P1(i,j)=P2(i,j) and if COMP(i,j)<(1−Tolerance), then the pixel P2(i,j)=P1(i,j). Thus, the pixels affected by X-ray interaction have been identified and removed. In the current actualization of this algorithm, three images are preferred and the Tolerance of deviation is set to 0.1. The corrected projections, P1* and P2*, can then be averaged arithmetically or geometrically to sum the information obtained by imaging the object at the specific orientation and to further increase the counting statistics in order to effectively improve the signal-to-noise ratio for the projection corresponding to that orientation. This is repeated for all orientations of the sample that are imaged.

The required number of projections acquired may be a function of image format and the feature of interest's size/contrast in the resulting projections. Although it can be appreciated that by increasing the number of projections acquired, one increases the quality of the reconstructed volume, a detailed discussion on the theoretically required minimum number of projections for faithful reconstruction of a given object under a set of given scan parameters will be omitted. However, because acquiring a sufficient number of projections is often necessary to realize the full functionality of this and any computed tomography tool, a rule of thumb based on simple angular dependence of volume sampling is provided in Table 1 below. The recommended minimum number of projections can be given as a function of image format:

TABLE 1

| Image Format | Approximate Number of Unique Periodic Projections over at least 180° for Faithful Reconstruction |
| --- | --- |
| 512 × 512 | 361 |
| 1024 × 1024 | 721 |
| 2048 × 2048 | 1441 |

During the correction of the projections performed in step 904, a third step is simultaneously performed within the data correction algorithm, as indicated in step 906. Step 906 may be a standard sensor calibration, such as a CCD correction, which in the provided formula corresponds to a CCD sensor correction. The CCD is sensitive to thermal variations, and contains an electronic background. To eliminate these influences from the acquired projections, one or more 'Dark' exposures are taken of the same exposure length as the projection exposure, averaged together if greater than one in number, and subtracted off of any exposure taken with the sensor exposed to signal. The images of the object's X-ray projections acquired during the scan also contain variation which can be attributed to sensor sensitivity non-uniformity, and optical non-uniformity such as, for example, optical vignetting or scintillator defects. These aspects of the detector system can be corrected by acquiring an identical image as that taken for the object's X-ray projection, only without any object in place, called a 'reference' or 'flat' frame. These frames are acquired periodically, and matched to the object's X-ray projection using background counts and time of acquisition, before performing the arithmetic correction outlined in the data processing flowchart for step 906. As already mentioned, steps 904 and 906 can be performed within the same algorithm.

The fourth step in the data processing routine corrects for any variation in the incident X-ray beam's intensity from projection-to-projection, however slight, as indicated in step 908. In this step, it is assumed that every projection contains some specific portion of the image which is always capturing purely incident X-ray intensity (i.e., air), or no object. The mean intensity in this portion of the image can be used to normalize all projections with one-another. The global mean is calculated by measuring the mean in this portion of the image sensor for the entire projection stack, and each projection is scaled relative to the ratio of the global mean to the local mean for every pixel in the projection corresponding to the local mean. The result is less variation in object intensity from projection to projection on the account of X-ray beam incident intensity.

In order to eliminate rings, which are reconstruction artifacts that arise from 'dead' image sensor elements, a fifth correction step may performed, as indicated in step 910.

Step 910 aims to find pixels which are significantly different from their surrounding pixels, and present in all frames: In other words, dead imaging elements. The principle of step 910 is that by identifying these pixels, the 'dead' value can be replaced with a value more representative of the object being image, such as the median value of a neighborhood around the dead pixel, which will change among orientations and will be, to some extent, representative of the objects transmitted X-ray intensity at the position corresponding to the dead pixel, which would otherwise be lost entirely. The dead pixels are identified by taking the mean and the standard deviation of all the pixels' values within a certain distance from the every pixel in every projection. If the central pixel's value is outside of a tolerance-factor number of standard deviations from the mean of that pixel's neighborhood, it is identified as a dead or unresponsive imaging element, and the value of the central pixel is replaced with the median value of the central pixel's neighborhood.

The sixth step in the projection correction processing is an optional step that may required if the X-ray beam was interrupted during the scan for whatever reason, including a re-centering or adjustment of the X-ray generating electron beam, as indicated in step 912. When the X-ray is interrupted and resumed, a slight shift in the object projection may be present between projections. To correct for this circumstance, the last object's orientation acquired before adjustment is re-acquired before continuing on to new projections. The purpose of re-acquiring the same projection, 'PX', is to use this image to align projections P1 to PX with projections PX+1 to PN, where P1 is the first projection in the last sequence, PX is the last projection in the last sequence, and PN is the last projection in the next sequence. A transformation, T, can be constructed which, when applied to PX' (the same projection after beam interruption), returns the image PX. This transformation is determined by minimizing an energy functional between PX and PX'; In the current actualization of this system's prototype, the energy function used is a sum-of-square-differences between PX and PX'*T as T varies. The transformation can be considered a rigid transformation only, as rotations and shear will not be produced by a shift in the X-ray generation point, as a translation would. The transformation, T, is then applied to all images in the succeeding imaging round, that is, projections PX+1 to PN.

After the projections have been corrected, additional reconstruction can be performed. The seventh step in the processing workflow is to identify the column in the projections about which the projections are rotating during the tomography scan, as indicated in step 914. Although this can in theory be performed using only two projections, 180° apart, it may be more practical to calculated by iteratively reconstructing the central slice of the object using finite increments of the rotation axis value across a range of reasonable rotation axis values, inspecting the reconstructed planes for minimal artifact presence, and adopting the value which produces the most faithful reconstruction to apply to all slices in the scanned object's reconstruction. The geometry of the scan, including the aforementioned rotation axis position, X-ray-source-to-rotation-axis distance and X-ray-source-to-detector distance can then be incorporated into the reconstruction algorithm. The stack of projections may also be incorporated into the reconstruction algorithm to back-project the attenuation values into a calculated volumetric mesh corresponding to the sample. Specific to lab-scale instruments, the result is a three-dimensional array of values which is defined by the same image format as the projections were acquired in, wherein each volume element, or 'voxel', contains the average X-ray attenuation coefficient of the material components that reside in that voxel over the X-ray energy spectrum produced by the X-ray source's braking-radiation mechanism.

At this point, the reconstructed volume may be resized to correspond to the resolution of the imaging system used in the acquisition of this data field, as is performed in the eighth step of the suggested processing sequence, indicated in step 916. If applicable, step 916 effectively de-noises the image at no cost to image resolution. After reconstruction, the image may be downsized to the format of the targeted resolution, as indicated in step 918.

The first nine steps of the example twelve step method have been outlined. The remaining three steps may or may not be necessary depending on the goals of the tomography, the sample, and the scan parameters used. In cases of lab-scale tomography where features are of interest within an overlying metallic object, it may be necessary to remove beam-hardening artifacts which arise due to the interplay between the very heavily X-ray attenuating metal and the low-energy end of the polychromatic X-ray spectrum used for imaging which are attenuated primarily at the surface. One effort that can be made to reduce this artifact's prominence while in the acquisition stage is to use a pre-hardening X-ray attenuating filter, such as the half-value-layer commonly used in medical computed tomography scanning procedures. A filter of this sort attempts to attenuate a large degree of the lower energy X-rays and a small degree of the high energy X-ray, effectively reducing the band-width of the polychromatic beam. In the case of a half-value-layer filter, the thickness of the filter material used is increased until the filtered X-ray beam has a total intensity equal to half of the unfiltered beam, and it is understood that this is achieved by attenuating primarily the low energy X-rays. Because low-energy X-rays are more readily attenuated than high-energy X-ray, the surface of a metal object will appear more heavily attenuating than the interior, giving rise to a 'bright' periphery of the reconstructed object, which is known as the beam-hardening artifact.

Beam hardening may corrected for according to step 920 of the data processing sequencing flowchart. Beam hardening correction is characterized by darker objects reconstructed interior than its exterior, and the values can be scaled relative to one another depending on how far an object pixel is from the surface. The values in the reconstructed plane are selected, for example, by performing a global threshold of the values in the reconstructed image that correspond to the object which is exhibiting the beam hardening artifact, and the selection is binarized. Each pixel corresponding to an object value in the binarized image can then be assigned a Euclidean distance to the non-object value in the binarized image, resulting in a Euclidean distance map of the reconstructed plane. The Euclidean distance map may contains information on how far each object pixel is from the exterior surface of the object. The Euclidean distance map can then be used to scale the values in the original reconstructed plane such that the object's reconstructed image plane contains similar values at all pixels in the object corresponding to a certain phase.

The eleventh step in the example processing, specific to the goal of volume segmentation, is a de-noising of the volume by performing 3D Gaussian filtering (blurring), using a kernel size which is suitable for producing a volume of the desired smoothness, as indicated in step 922. The twelfth step in the recommended processing routine is the image segmentation, where the segmentation method used is one that can segment the desired features most accurately with a minimum labor requirement, as indicated in step 924

Figure 10:
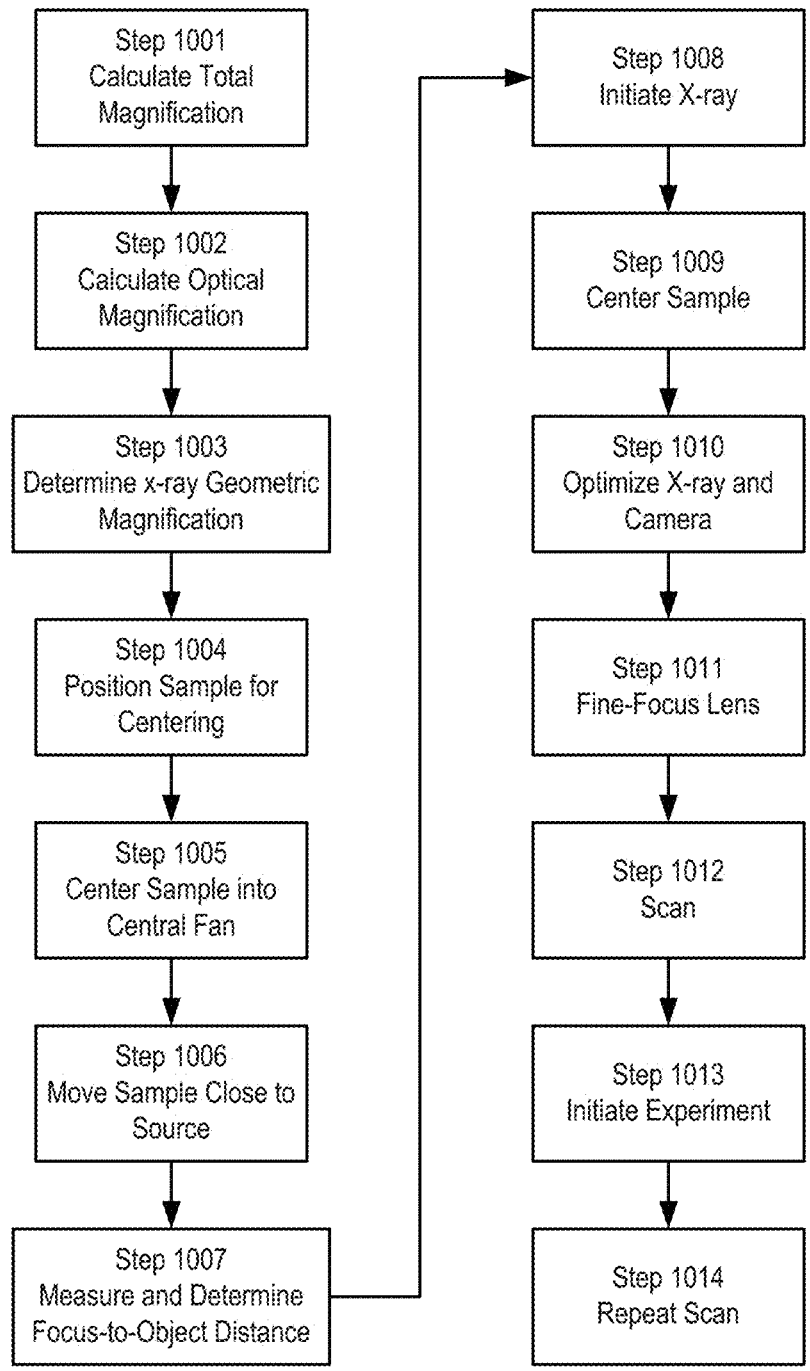
FIG. 10 is a flowchart setting forth exemplary steps of a method for scanning with an XCT system.

An example of a process for setting up a scan for optimized reconstruction accuracy using the XCT system 100 of the present invention is shown in FIG. 10. The process starts with calculating the total magnification, $M_{system}$, needed to fill the field of view for the sample of interest, as indicated at step 1001. The optical magnification, $M_{optical}$, to be implemented is then calculated, as indicated at step 1002. The X-ray geometric magnification needed is then determined, as indicated at step 1003. As one example, the geometric magnification can be determined using the following equation:

$$M_{system} = M_{optical} \times M_{x-ray} \quad (7)$$

The sample is then roughly positioned on the centering stages, as indicated at step 1004. A better rough position minimizes the footprint of the centering stages after centering. The sample is then centered into the center of the X-ray beam using a z-stage, as indicated at step 1005. The sample stack is then moved using the long range stages so that the sample is as close to the X-ray source as possible, as indicated at step 1006, thereby maximizing the flux through the sample.

Figure 11:
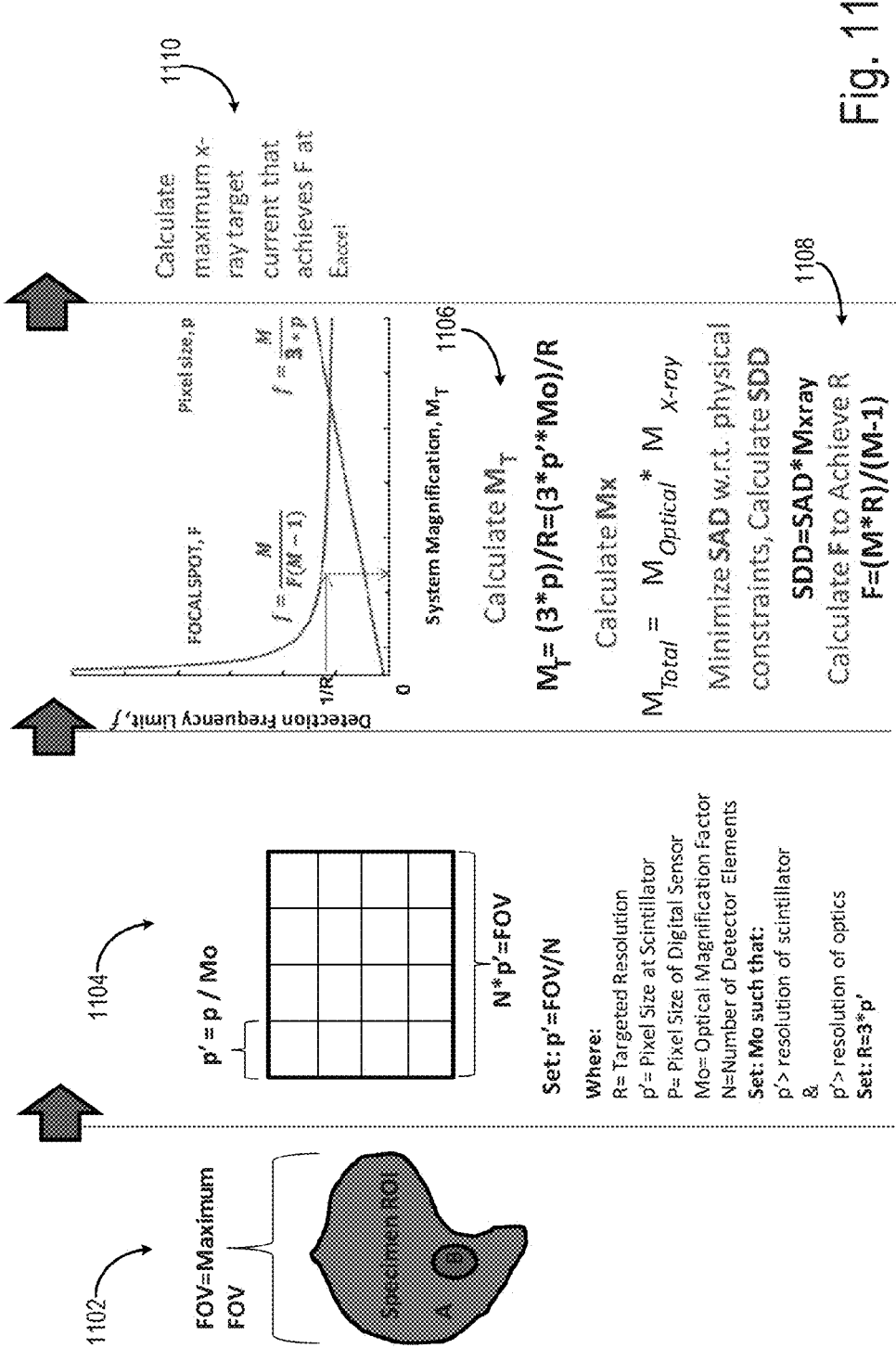
FIG. 11 is a flowchart setting forth exemplary steps of a method for optimizing some parameters for resolution.

Steps 1001-1006 may also be performed as shown in FIG. 11, steps 1102-1110. The sample field of view (FOV) is determined, and the X-ray energy and the X-ray accelerating voltage ($E_{accel}$) are calculated, as indicated in step 1102. The X-ray energy is used to determine the maximum feature contrast using $(\mu/\rho)_a/(\mu/\rho)_b$ as a function of X-ray energy. The X-ray accelerating voltage is also used to achieve maximum intensity at the X-ray energy. The targeted resolution (R) and optical magnification factor (Mo) may also be calculated, as shown in step 1104. The system magnification (MT) is calculated, as indicated in step 1106, and the total system magnification ($M_{Total}$) along with the optical magnification ($M_{optical}$) are used to calculated the X-ray magnification ($M_{x-ray}$) and then the focal spot (F) in step 1108. Using the above calculated values, the maximum X-ray target current that achieves the focal spot at the accelerating voltage is calculated in step 1110.

Next, the minimum focus-to-object distance is measured at step 1007. For example, the focus-to-object distance ("FOD") can be determined using the following equation:

$$M_{x-ray} = \frac{FDD}{FOD}; \quad (8)$$

where FDD is the focus-to-detector distance and $M_{x-ray}$ is the geometric magnification determined in step 1003. The detector (scintillator) is then positioned using the long range stages.

The X-ray source can optionally be energized with a low power to acquire a sample profile, as indicated at step 1008. The sample is then centered using the sample rotation stage 104 and centering stages, as indicated at step 1009. As indicated at step 1010, the XCT system 100 may optimize X-ray energy and power and camera 301 exposure length with respect to detected feature contrast and total scan time. Fine-focusing of the lens 324 onto the scintillator screen can be performed using the linear focusing stage, as indicated at step 1011. A scan of the sample can be initiated at step 1012, which may include initiating an in situ experiment at step 1013. In step 1014, the scan can be repeated.

The present invention has been described in terms of one or more preferred embodiments, and it should be appreciated that many equivalents, alternatives, variations, and modifications, aside from those expressly stated, are possible and within the scope of the invention.

The invention claimed is:

1. A modular X-ray computed tomography system comprising:
    a base;
    an interchangeable X-ray source coupled to the base and configured to emit an X-ray beam towards a sample positioned in the modular X-ray computed tomography system, wherein the interchangeable X-ray source is one of a plurality of different X-ray sources configured to be interchangeably coupled to the base;
    a sample rotation stage coupled to the base and configured to receive a sample and to position the sample within a field-of-view of the interchangeable X-ray source;
    an X-ray detection system coupled to the base and comprising:
        at least one interchangeable X-ray detector configured to acquire data as X-rays impinge on the at least one interchangeable X-ray detector, wherein the at least one interchangeable X-ray detector is one of a plurality of different X-ray detectors configured to be interchangeably coupled to the X-ray detection system;
        a port configured to receive the at least one interchangeable X-ray detector; and
    at least one computing system in communication with the X-ray detection system and configured to receive the data from the X-ray detection system and to reconstruct an image of the sample from the data.

2. The modular X-ray computed tomography system as recited in claim 1, wherein the at least one interchangeable X-ray detector comprises at least one of a scintillator and a photon counting detector.

3. The modular X-ray computed tomography system as recited in claim 2, wherein the scintillator is characterized by a material or device capable of producing photons of a lower energy than the X-rays absorbed by the X-ray detector and independent of an absorption efficiency.

4. The modular X-ray computed tomography system as recited in claim 3, wherein a quantity of the photons produced by the scintillator are dependent on an intensity of incident X-ray photons.

5. The modular X-ray computed tomography system as recited in claim 1, wherein the X-ray detection system is a lens-coupled X-ray detection system and further comprises a lens that is optically coupled to the at least one interchangeable X-ray detector.

6. The modular X-ray computed tomography system as recited in claim 1, wherein the X-ray detection system is a fiber optically-coupled X-ray detection system and further comprises a fiber optic assembly optically coupled to the at least one X-ray detector.

7. The modular X-ray computed tomography system as recited in claim 6, wherein the fiber optic assembly is configured to couple at least one photo-electronic sensor elements to at least one scintillating X-ray detectors.

8. The modular X-ray computed tomography system as recited in claim 1, wherein the interchangeable X-ray source includes a microfocus X-ray source capable of emitting X-rays from a micrometer-sized target area.

9. The modular X-ray computed tomography system as recited in claim 1, wherein the sample rotation stage is configured to rotate without physical distortion and provides precise positioning of the sample being imaged.

10. The modular X-ray computed tomography system as recited in claim 1, wherein the sample rotation stage includes X and Y centering stages to center the sample on the sample rotation stage to at least one of maximize a field of view and increase a resolution.

11. A method of image reconstruction using a modular X-ray computed tomography system, the method comprising:
- receiving a sample on a sample rotation stage coupled to a base;
- positioning the sample on the sample rotation stage within a field-of-view of an interchangeable X-ray source;
- emitting, from the interchangeable X-ray source, an X-ray beam towards a sample positioned in the modular X-ray computed tomography system, wherein the interchangeable X-ray source is one of a plurality of different X-ray sources configured to be interchangeably coupled to the base;
- acquiring data, using at least one interchangeable X-ray detector coupled to the base, as X-rays impinge on the at least one interchangeable X-ray detector, wherein the at least one interchangeable X-ray detector is one of a plurality of different X-ray detectors configured to be interchangeably coupled to a X-ray detection system; and
- receiving the using at least one computing system in communication with the X-ray detection system, from the X-ray detection system to reconstruct an image of the sample from the data.

12. The method of image reconstruction as recited in claim 11, wherein the at least one interchangeable X-ray detector comprises at least one of a scintillator and a photon counting detector.

13. The method of image reconstruction as recited in claim 12, wherein the scintillator is characterized by a material or device capable of producing photons of a lower energy than the X-rays absorbed by the X-ray detector and independent of an absorption efficiency.

14. The method of image reconstruction as recited in claim 13, wherein a quantity of the photons produced by the scintillator are dependent on an intensity of incident X-ray photons.

15. The method of image reconstruction as recited in claim 11, wherein the X-ray detection system is a lens-coupled X-ray detection system and further comprises a lens that is optically coupled to the at least one interchangeable X-ray detector.

16. The method of image reconstruction as recited in claim 11, wherein the X-ray detection system is a fiber optically-coupled X-ray detection system and further comprises a fiber optic assembly optically coupled to the at least one X-ray detector.

17. The method of image reconstruction as recited in claim 16, wherein the fiber optic assembly is configured to couple at least one photo-electronic sensor elements to at least one scintillating X-ray detectors.

18. The method of image reconstruction as recited in claim 11, wherein the interchangeable X-ray source includes a microfocus X-ray source capable of emitting X-rays from a micrometer-sized target area.

19. The method of image reconstruction as recited in claim 11, wherein the sample rotation stage is configured to rotate without physical distortion and provides precise positioning of the sample being imaged.

20. The method of image reconstruction as recited in claim 11, wherein the sample rotation stage includes X and Y centering stages to center the sample on the sample rotation stage to at least one of maximize a field of view and increase a resolution.

* * * * *